United States Patent [19]
Imoto

[11] Patent Number: 5,879,312
[45] Date of Patent: Mar. 9, 1999

[54] HARDNESS TESTER FOR LIVING BODY

[75] Inventor: Toshiyuki Imoto, Kyoto, Japan

[73] Assignee: Imoto Machinery Co., Ltd., Kyoto, Japan

[21] Appl. No.: 960,287

[22] Filed: Oct. 29, 1997

[30] Foreign Application Priority Data

Nov. 8, 1996 [JP] Japan .................................. 8-313137
Sep. 12, 1997 [JP] Japan .................................. 9-268112

[51] Int. Cl.$^6$ ........................................................ A61B 5/00
[52] U.S. Cl. .............................................. 600/587; 73/81
[58] Field of Search ................................... 600/550, 552, 600/553, 587; 73/81, 82

[56] References Cited

U.S. PATENT DOCUMENTS

| | | | |
|---|---|---|---|
| 4,159,640 | 7/1979 | Leveque et al. | 73/81 |
| 4,217,912 | 8/1980 | Hubmann et al. | 128/774 |
| 4,331,026 | 5/1982 | Howard et al. | 73/81 |
| 4,503,865 | 3/1985 | Shishido | 128/774 |
| 5,305,633 | 4/1994 | Weissenbacher et al. | 73/82 |

FOREIGN PATENT DOCUMENTS 51-84684 7/1976 Japan .
U-3 028 586 6/1996 Japan .

*Primary Examiner*—Max Hindenburg
*Attorney, Agent, or Firm*—Oliff & Berridge, PLC

[57] ABSTRACT

In a hardness tester according to the present invention, an indentor is urged by an indentor spring and moves against the indentor spring when pressed against an object part of a living body. The indentor is inserted in a sleeve which is urged by a sub spring weaker than the indentor spring and moves against the sub spring when pressed against the part of the living body. A converter converts an amount of movement of the indentor into an electrical signal. A trigger generates a trigger signal when the sleeve has moved by a predetermined amount. A control unit carries out a process when receiving the trigger signal, the process including steps of: receiving the digital signal from the converter; displaying the amount of movement of the indentor on a display; storing the amount in a memory unit; calculating a difference in hardness of the part of the living body between a relaxed condition and a strained condition; and displaying the difference on the display.

7 Claims, 10 Drawing Sheets

HARDNESS TESTER FOR LIVING BODY

The present invention relates to a hardness tester for measuring the hardness of a part of a living body, e.g. the hardness of a living tissue such as muscles, skin, or internal organs.

BACKGROUND OF THE INVENTION

One such conventional hardness tester, which was proposed by the inventor of the present invention, is disclosed in the Publication of the Japanese Utility Model Registration No. 3,028,586. The configuration and operation of the hardness tester is as follows.

Referring to FIGS. 9 and 10, the hardness tester includes a first unit 53 and a second unit 56. The first unit 53 has a main leg 52, which is urged downward by a compression spring 51 and moves upward against the compression spring 51 when pressed against an object part of a living body (e.g. a living tissue), and a display unit 62, which digitally displays an amount of displacement of the main leg 52. The second unit 56 has a pair of side legs 55, 55 provided on both sides of the main leg 52. The side legs 55, 55 are urged downward by tension springs 54, 54 weaker than the compression spring 51 and move upward against the tension springs 54, 54 when pressed against the object part. The second unit 56 further includes a retaining mechanism 50 for retaining the amount of displacement displayed by the display unit 62 at the moment the side legs 55, 55 have moved by a predetermined amount.

In the retaining mechanism 50, a module plate 41 with a rubber plate 42 fixed on its back is mounted on the top of the main leg 52, and is guided by a pair of guide rails 63 to slide vertically. A slider 58 which slides vertically on a pair of guide poles 57, 57 is mounted on the top of the pair of side legs 55, 55. A notched step part 43 having a reversed-U shape is formed in the slider 58 in opposition to the rubber plate 42. The notched step part 43 has a notch 44 formed at the center of the slider 58 and a pair of steps 45 formed on both sides of the notch 44 at the back of the slider 58, where each step 45 has a sloped face 59 at its lower end. A stopper pin 48 having a serrated face 46 at its front end and a cross pin 47 in its body, is urged by a compression spring 49 toward the rubber plate 42 so that the front end is posed in the notch 44 of the notched step part 43 and the cross pin 47 contacts with the step 45 at both sides.

In the above-described hardness tester, when the main leg 52 and the two side legs 55, 55 are pressed against the object part, the legs move upward against the springs. Here, the movement of the slider 58 is larger than that of the module plate 41 since the tension springs 54, 54 for the side legs 55, 55 are weaker than the compression spring 51 for the main leg 52.

When the slider 58 ascends to a preset height, the cross pin 47 of the stopper pin 48 is displaced off the steps 45 of the notched step part 43. At this moment, the stopper pin 48 is activated by the compression spring 49 to plunge forward, as shown in FIG. 10, so that the pin 48 presses the rubber plate 42 at the back of the module plate 41 with its front end. Thus, the module plate 41 is held under compression against a scale 60.

In the above state, the module plate 41 is securely fixed at the position since the serrated face 46 provided at the front end of the stopper pin 48 embeds itself into the rubber plate 42. The hardness of the object part in contact with the main leg 52 is digitally displayed by the display unit 62. In this state, the stopper pin 48 is pressed against the rubber plate 42 not only by the compression spring 49 but also by the tension springs 54, 54 since the cross pin 47 is pressed forward by the sloped faces 59 of the lower front ends of the steps 45 activated by the tension springs 54, 54.

When the knob 64 at the back of the casing is pulled against the compression spring 49, the serrated face 46 at the front end of the stopper pin 48 releases the rubber plate 42, so that the main leg 52 is activated by the compression spring 51 to return to its original position automatically and the digital display of the display unit 62 is also reset.

The above-described hardness tester of the Japanese Utility Model Registration No. 3,028,586, however, is accompanied by some problems as follow.

(1) Since the cross pin 47 of the stopper pin 48 is pressed against the slider 58 by the compression spring 49 (as shown in FIG. 10), the slider 58 encounters frictional resistance during the ascent so that the stress in the compression spring 51 for the main leg 52 is larger than theoretically estimated. Thus, the hardness of the object part cannot be measured accurately.

(2) After the hardness tester has been in use for a long time, the effective grip by the serrated face 46 on the surface of the rubber plate 42 by the stopper pin 48 becomes more difficult due to frequent abrasion. In this case, the main leg 52 is pushed back by the compression spring 51 even when the module plate 41 is clamped between the scale 60 and the stopper pin 48.

(3) The pressure mechanism for stopping the module plate 41 utilizes the stress of the compression spring 49. This requires such a large number of parts that errors may easily occur in assembling, which lowers the reliability of the measurement by the hardness tester. Furthermore, the hardness tester including many parts is not easy to operate.

(4) The main leg 52 and the side legs 55, 55 are each separated by a considerably large distance. Therefore, when the hardness of an uneven part of a living body or a part with a small radius of curvature is measured, a measurement error is inevitable.

Publication No. S51-84684 of the Japanese Unexamined Patent Application discloses another hardness tester including a cylindrical guard ring which is located by sliding onto the side of an indenting rod provided in the center of the lower part of the hardness tester. The configuration of this hardness tester, however, is very complicated since it utilizes a strain gauge, hall element, photoelectric element, or differential transformer to build up a system for detecting the displacement of the indenting rod electrically.

In addition, any of the conventional hardness testers has only one detection rod (penetrator, indentor, feeler, etc.). Therefore, during a measurement using the conventional hardness tester, the rod may easily tilt, resulting in an incorrect measurement result.

In measuring the hardness of a part of a living body, particularly, the measurement result easily changes even by a small displacement of the measurement point or by a small tilt of the detection rod. Therefore, when a hardness tester with a single detection rod is used to measure the hardness of an object point, it is necessary to measure the hardness of a plurality of points around the object point and take the average of the hardness at the points to obtain a reliable measurement result.

SUMMARY OF THE INVENTION

For solving the above problems, the present invention proposes a first hardness tester for a living body, which includes:

a) an indentor which is urged by an indentor spring and moves against the indentor spring when pressed against a part of the living body;

b) a sleeve in which the indentor is inserted and which is urged by a sub spring weaker than the indentor spring and moves against the sub spring when pressed against the part of the living body;

c) a converter for converting an amount of movement of the indentor into an electrical signal;

d) a trigger for generating a trigger signal when the sleeve has moved by a predetermined amount; and e) a control unit for carrying out a process when receiving the trigger signal, the process including steps of:
receiving the electrical signal from the converter;
displaying the amount of movement of the indentor on a display;
storing the amount in a memory unit;
calculating a difference in hardness of the part of the living body between a relaxed condition and a strained condition; and
displaying the difference on the display.

The present invention further proposes a second hardness tester for a living body, which includes a plurality of measurement units, each measurement unit comprising:

a) an indentor which is urged by an indentor spring and moves against the indentor spring when pressed against a part of the living body;

b) a sleeve in which the indentor is inserted and which is urged by a sub spring weaker than the indentor spring and moves against the sub spring when pressed against the part of the living body;

c) a converter for converting an amount of movement of the indentor into an electrical signal; and d) a trigger for generating a trigger signal when the sleeve has moved by a predetermined amount, where the measurement units are combined together so that all the lower ends of the indentors and the sleeves are aligned on the same plane, and the hardness tester further includes:

e) a control unit for carrying out a process when receiving the trigger signal, the process including steps of:
receiving the electrical signals from the converters of the measurement units;
taking an average of movements of the indentors measured by the measurement units corresponding to the plurality of points in proximity to an object point on the part of the living body;
displaying the average of movements of the indentors on a display;
storing the average in a memory unit;
calculating a difference in hardness of the part of the living body between a relaxed condition and a strained condition; and
displaying the difference on the display.

The third hardness tester of the present invention is a modification of the first or second hardness tester, wherein the converter includes a linear scale and an encoder for converting the amount of movement of the indentor into a digital signal.

The fourth hardness tester of the present invention is a modification of the first or second hardness tester, wherein the converter includes a displacement sensor for measuring the amount of movement of the indentor based on a change in the capacitance of a condenser.

The present invention further proposes a fifth hardness tester for a living body, which includes a plurality of measurement units, each measurement unit comprising:

a) an indentor for indenting a part of the living body;

b) a sleeve in which the indentor is inserted;

c) an urging mechanism for urging the indentor and the sleeve, where a stress on the indentor is larger than that on the sleeve; and d) a calculator for calculating a hardness of the part of the living body based on a difference between a displacement of the indentor and a displacement of the sleeve when pressed against the part of the living body, where the measurement units are combined together so that all the lower ends of the indentors and the sleeves are aligned on the same plane, and the hardness tester further includes:

e) an average calculator for taking an average of hardness measured by the measurement units at the plurality of points around an object point at one time.

BRIEF DESCRIPTION OF THE DRAWINGS

Preferred embodiments of the present invention will be detailed later, referring to the attached drawings wherein.

DETAILED DESCRIPTION OF PREFERRED EMBODIMENTS

Embodiment 1

Figure 1:
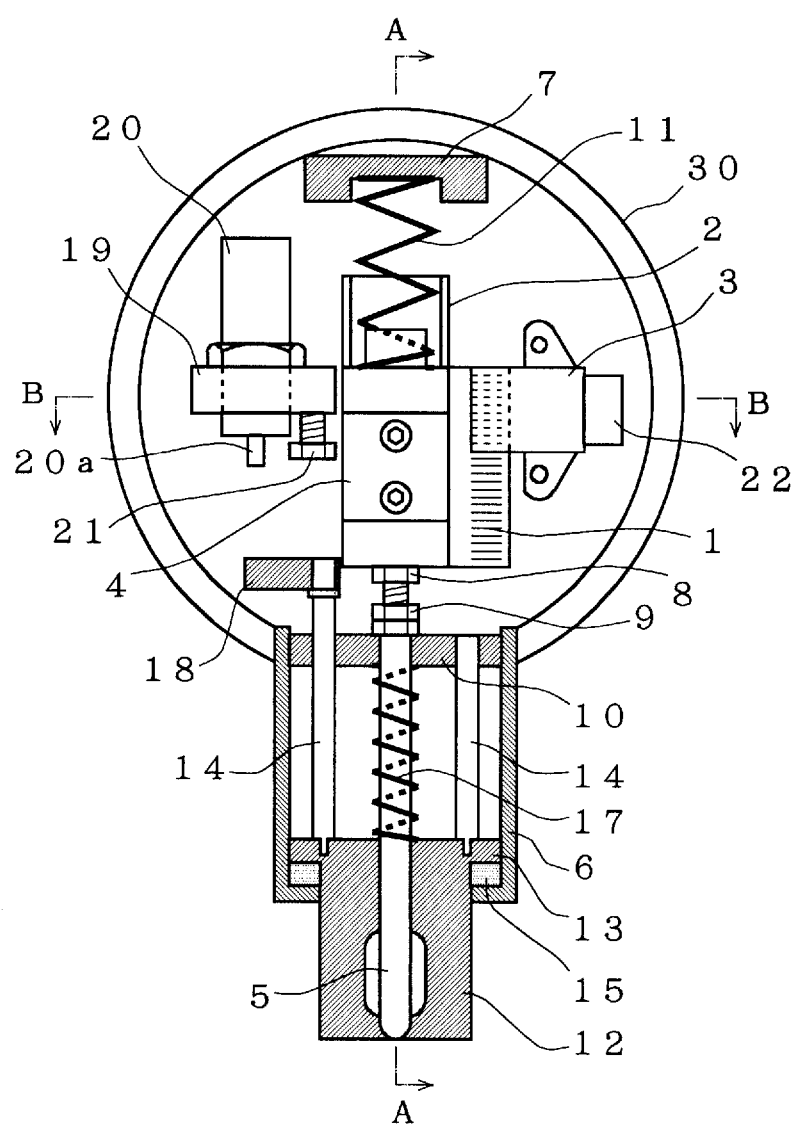
FIG. 1 is a back view of an inventive hardness tester with its back uncovered, part of which is shown as a sectional view.

An embodiment of the present invention is detailed below, referring to FIGS. 1–5.

In an inventive hardness tester shown in FIGS. 1–5, a linear scale 1 is vertically fixed on the front face of a scale fixation plate 4 which is mounted on the top of an indentor 5 disposed in the center of a casing 30. A linear guide 2 is provided inside the central part of the casing 30, whereby the linear scale 1 is guided to slide up and down. A longitudinal edge of the linear scale 1 is slidably inserted in a slit of an encoding module 3 provided inside of the side part of the casing 30.

Figure 2:
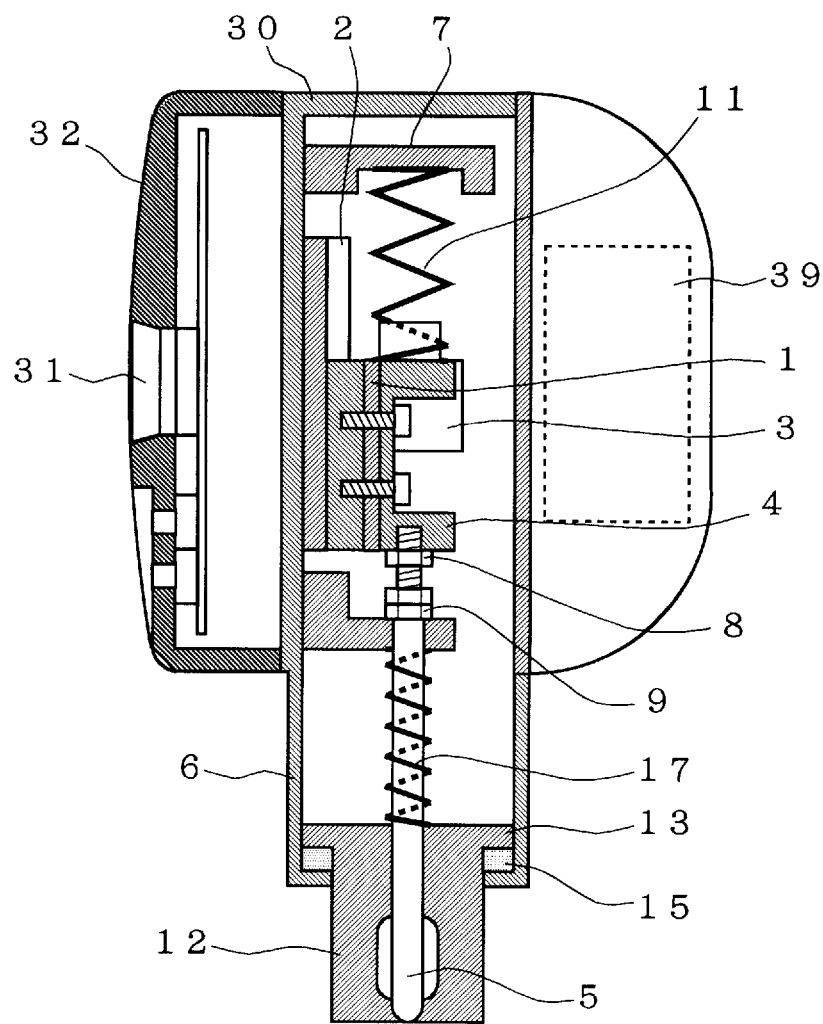
FIG. 2 is a vertical sectional view on line A—A of FIG. 1.
Figure 3:
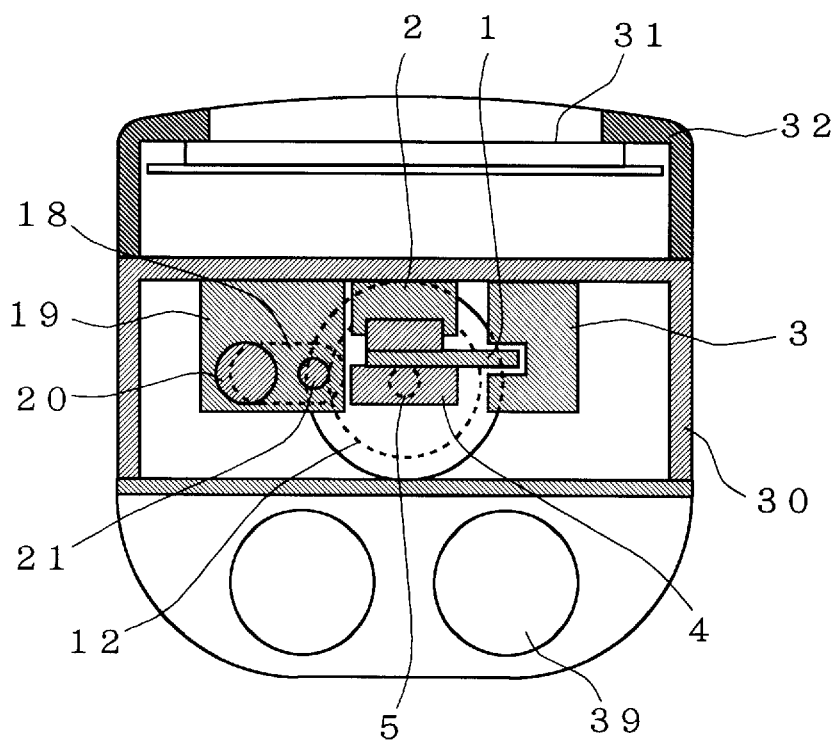
FIG. 3 is a horizontal sectional view on line B—B of FIG. 1.

The lower part of the indentor 5 is inserted into a sleeve 12 and protrudes through the lower end of the casing 30 together with the sleeve 12, as shown in FIG. 2. The indentor 5 is borne at its upper part by a supporting plate 10 disposed horizontally in the center of the casing 30. The fixation plate 4 is fixed at the top of the indentor 5 by a screw.

The numeral 8 denotes a lock nut for securing the screw connection between the indentor 5 and the scale fixation plate 4. When the lock nut 8 is loosened, the depth of the screwed-in part of the indentor 5 can be changed, whereby the protruding length of the indentor 5 and the stress of an indentor spring 11 can be regulated. The numeral 9 denotes a pair of control nuts for controlling the stress of the indentor spring 11. By changing the position of the control nuts 9, the stress of the indentor spring 11 and the protruding length of the indentor 5 can be controlled.

The indentor spring 11 is a compression spring disposed between the top of the scale fixation plate 4 and a spring holder 7 provided inside of the upper part of the casing 30, whereby the indentor 5 is urged downward.

The sleeve 12 is a cylindrical member having a diameter larger than that of the indentor 5, and is provided with a flange 13 at its upper end. The lower part of the sleeve 12 projects through a cylindrical part 6 of the casing 30. A pair of side rods 14 are provided located on both sides of the top face of the flange 13, which are borne at their upper parts by the supporting plate 10. The sleeve 12 is urged downward by a sub spring 17, a compression spring disposed between the upper face of the sleeve 12 and the lower face of the supporting plate 10, admitting the indentor 5 therethrough.

The numeral 15 denotes an O-ring disposed between the bottom of the cylindrical part 6 of the casing 30 and the flange 13 of the sleeve 12.

Referring to FIG. 1, a switch activating plate 18 fixed to the upper end of the left side rod 14 extends horizontally to a position right under a switch 20.

The switch 20 is mounted on a switch fixation plate 19 disposed inside of the back of the casing 30, where the vertical position of the switch 20 can be varied. When the switch activating plate 18 contacts with the tip of a switch plunger 20a as a result of an upward movement of the side rod 14, the switch 20 sends a trigger signal to a limit controller 23 in a calculation unit 22 (see FIG. 5). On receiving the trigger signal, the amount of movement of the indentor 5 measured by the encoding module 3 is stored in a memory-A 25 and the digital data displayed on an LCD panel display 31 is retained (see also FIG. 5).

The numeral 21 denotes a stopper whose vertical position can be adjusted vertically. The stopper 21 prevents the switch activating plate 18 from exerting an excessive force on the switch 20 when the sleeve 12 is pushed upward.

Figure 4:
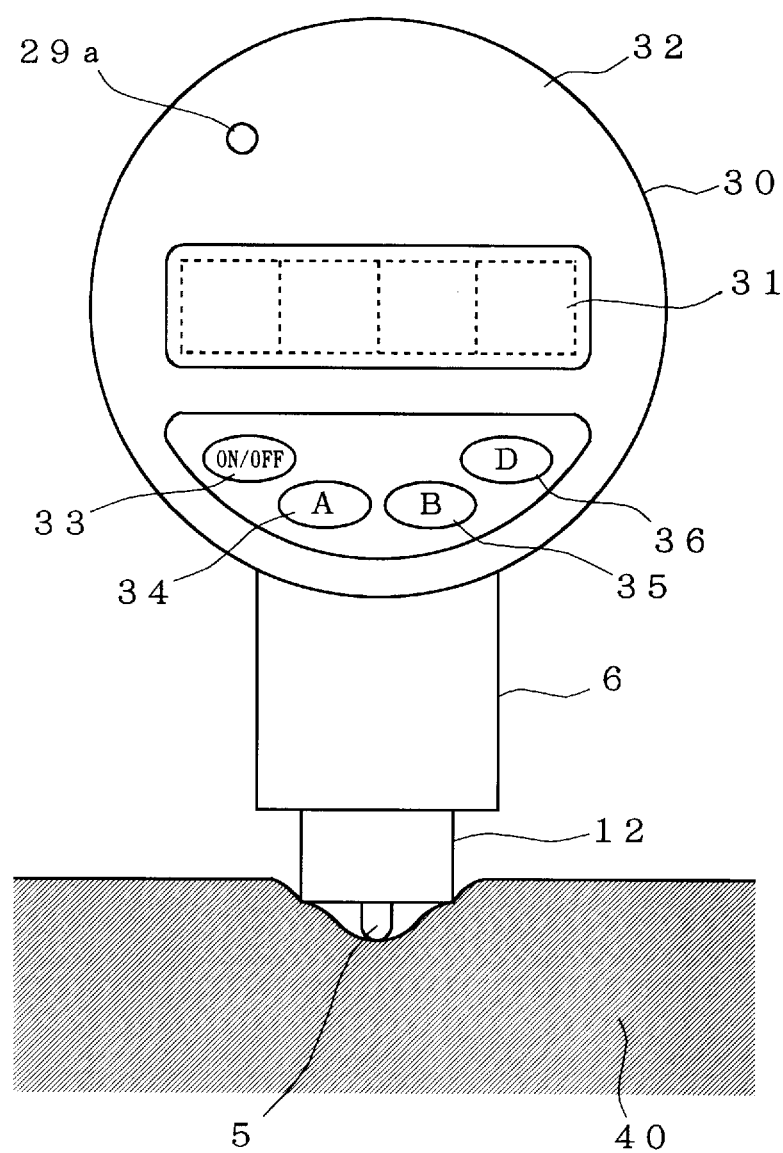
FIG. 4 is a front view of the hardness tester of FIG. 1.
Figure 5:
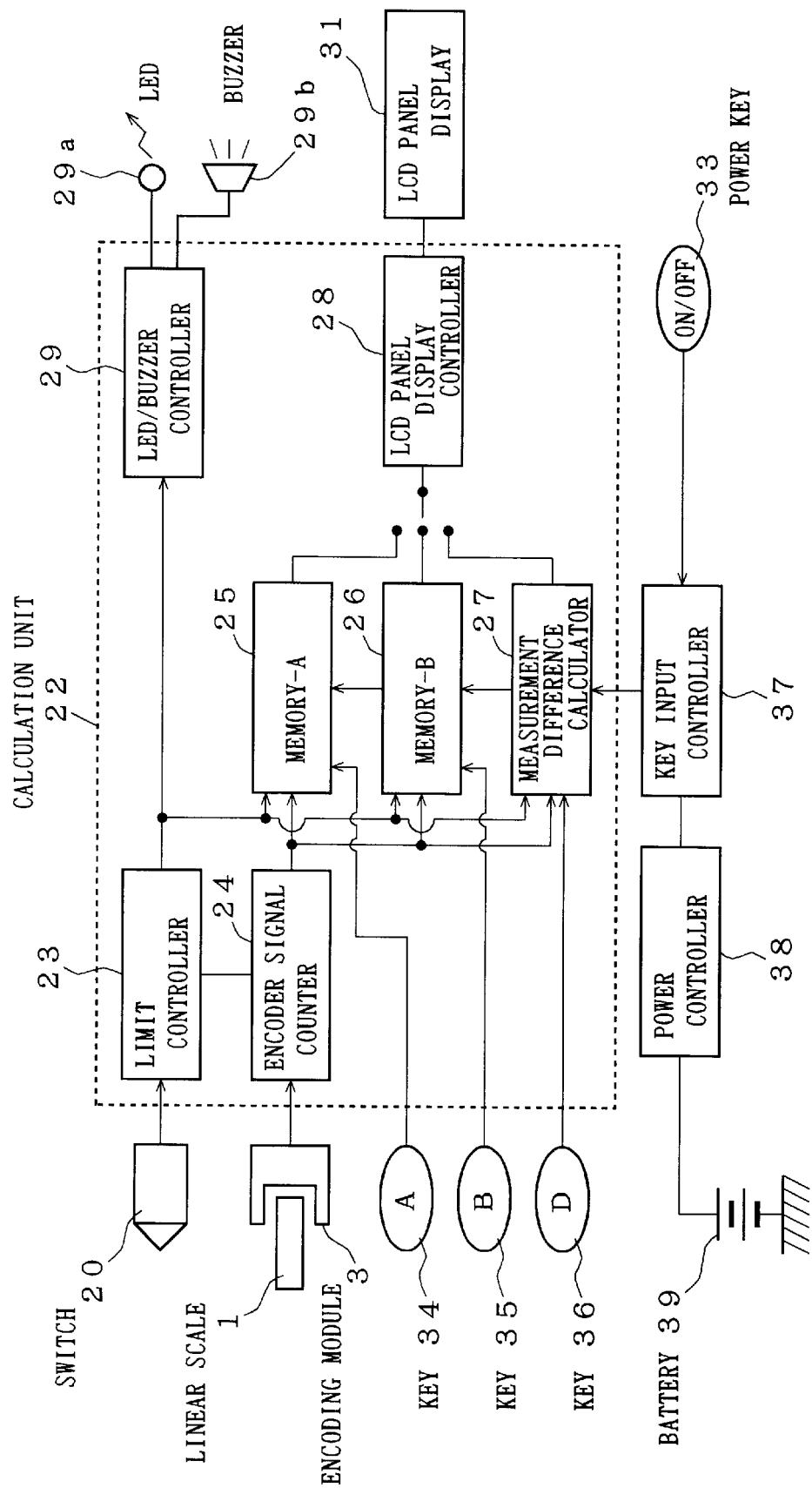
FIG. 5 is a block diagram of an example of an electrical system of the hardness tester of FIG. 1.

FIG. 5 shows the electrical system including a calculation unit 22. The calculation unit 22 includes: the limit controller 23 for receiving a signal from the switch 20; an encoder signal counter 24 for receiving a signal from the encoding module 3; the memory-A 25; a memory-B 26; a measurement difference calculator 27; an LCD (Liquid Crystal Display) panel display controller 28; and an LED (Light Emitting Diode)/buzzer controller 29. Output signals of the limit controller 23 and the encoder signal counter 24 are sent to the memory-A 25, the memory-B 26 and the measurement difference calculator 27. Output data of these three elements are sent to the LCD panel display controller 28, which displays the data on the LCD panel display 31 provided on a front cover 32 (see FIG. 4).

The LED/buzzer controller 29 activates an LED 29a and a buzzer 29b, both provided on the casing 30, when the switch 20 is triggered by the switch activating plate 18, thus informing the user that the sleeve 12 has moved upward by a predetermined amount. The LED/buzzer controller 29, however, is optional in the present invention.

The numeral 37 denotes a key input controller for controlling the on/off of the power supply to the measurement difference calculator 27 in the calculation unit 22. The numeral 38 denotes a power controller provided between the key input controller 37 and a battery 39 disposed at the back of the casing 30.

Referring to FIG. 4, the LCD panel display 31 is disposed at the center of the front cover 32 and four keys 33–36, including a power key 33, are disposed under the LCD panel display 31. The four keys 33–36 are connected with the key input controller 37, the memory-A 25, the memory-B 26 and the measurement difference calculator 27, respectively, as shown in FIG. 5.

In the present embodiment, the amount of movement of the indentor 5 is measured using the encoding module 3 which detects the movement of the linear scale 1 mounted on the upper end of the indentor 5 and generates a signal corresponding to the amount of movement. It should be appreciated that the amount of movement may be measured using other elements such as a displacement sensor utilizing a change in the capacitance, a vibration sensor, a load cell, etc.

Embodiment 2

Figure 6:
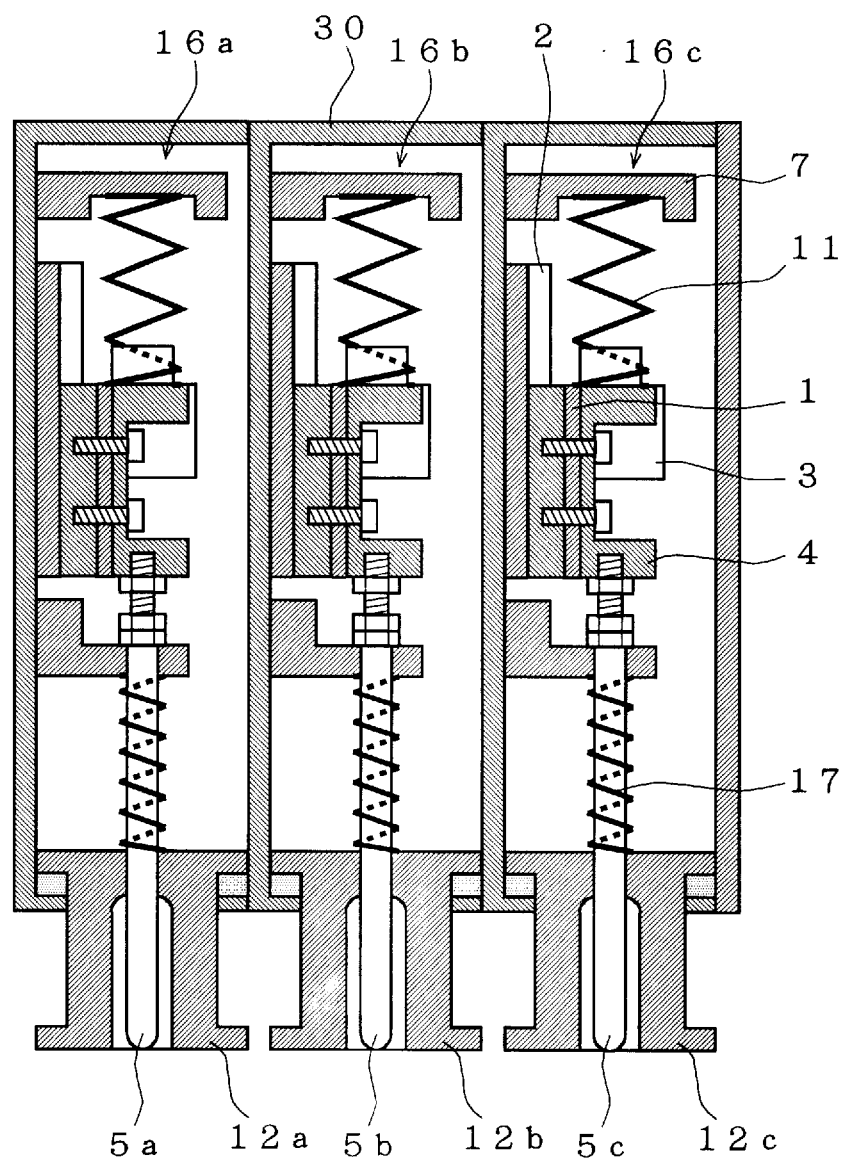
FIG. 6 is a vertical sectional view of another inventive hardness tester, viewed from the side.

FIG. 6 is a vertical sectional view of another inventive hardness tester, viewed from the side. The hardness tester includes three measurement units 16a, 16b and 16c. In each measurement unit, an indentor 5 is urged by an indentor spring 11, and the indentor 5 moves against the indentor spring 11 when pressed against an object part of a living body (e.g. a living tissue). The indentor 5 is inserted in a sleeve 12 which is urged downward by a sub spring 17 weaker than the indentor spring 11. The sleeve 12 moves on the indentor 5 against the sub spring 17 when pressed against the object part. A converter unit includes a linear scale 1 and an encoding module 3 for converting the amount of movement of the indentor 5 into digital signal. A switch 20 generates a trigger signal when the sleeve 12 has moved by a predetermined amount. The measurement units are combined together so that all the lower ends of the indentors 5a, 5b and 5c and the sleeves 12a, 12b and 12c are aligned to form a straight line on the same plane.

Apart from the measurement units as described above, a common control unit is provided wherein other elements of the hardness tester such as the LCD panel display 31, the battery 39, the calculation unit 22, etc., are installed. The calculation unit 22 in the present embodiment has an additional function of taking the average of measurement values obtained by the three measurement units, respectively, and displaying the average on the LCD panel display 31 digitally.

It should be noted that the above number of the measurement units, i.e. three, is a mere example and the number may be any number larger than one. Further, as for the alignment of the lower ends of the indentors and the sleeves, the alignment may take a cross-like form, for example, instead of the straight-line form.

Embodiment 3

Figure 7:
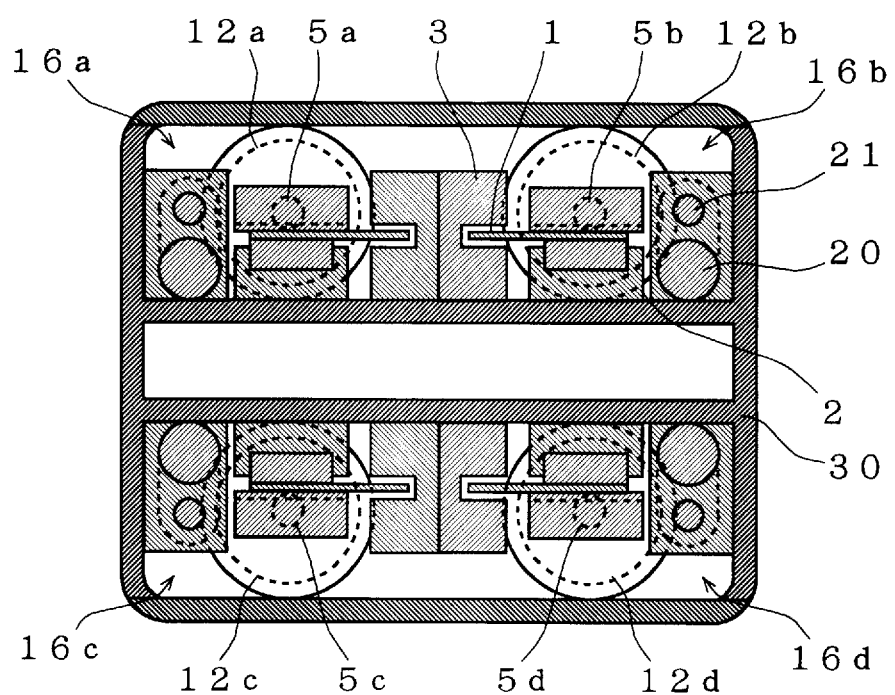
FIG. 7 is a horizontal sectional view of another inventive hardness tester, viewed from the top.

FIG. 7 is a cross sectional view of another inventive hardness tester, viewed from the top. The hardness tester includes four measurement units 16a, 16b, 16c and 16d. In each measurement unit, an indentor 5 moves against an indentor spring 11 for urging the indentor 5 downward when pressed against an object part of a living body. The indentor 5 is inserted in a sleeve 12 which is urged downward by a sub spring weaker than the indentor spring 11 and moves against the sub spring 17 when pressed against the object part. A converter unit includes a linear scale 1 and an encoding module 3 for converting the amount of movement of the indentor 5 into a digital signal. A switch 20 generates a trigger signal when the sleeve 12 has moved by a predetermined amount. The measurement units are combined together so that all the lower ends of the indentors 5a, 5b, 5c and 5d the sleeves 12a, 12b, 12c and 12d are aligned to form a square surrounding a central point on the same plane.

Apart from the measurement units as described above, a common control unit is provided wherein other elements of the hardness tester such as the LCD panel display 31, the battery 39, the calculation unit 22, etc., are installed. The calculation unit 22 in the present embodiment has an additional function of taking the average of measurement values obtained by the four measurement units, respectively, and displaying the average on the LCD panel display 31 digitally.

It should be noted that the above number of the measurement units, i.e. four, is a mere example and the number may be any number larger than two. When, for example, five measurement units are used, it is preferable to dispose four of them to form a square as described above and to dispose the fifth measurement unit at the center of the square.

When a plurality of measurement units are combined together as described above, it is preferable that the casing has such a shape and structure that it is easy to hold and to manipulate in the measurement.

In a hardness tester as described in the above embodiment 2 or 3, hardnesses of a plurality of points in proximity to an object point are measured at one time, and the average of the hardness is calculated. By such a hardness tester, the hardness of an object point of a living body is measured more easily and with less time and labor than using a conventional hardness tester having only one detection rod. It should be appreciated that the above effect is obtained even when the detailed configuration of the measurement unit is different from that of the hardness tester described referring to FIGS. 1–5.

Figure 8:
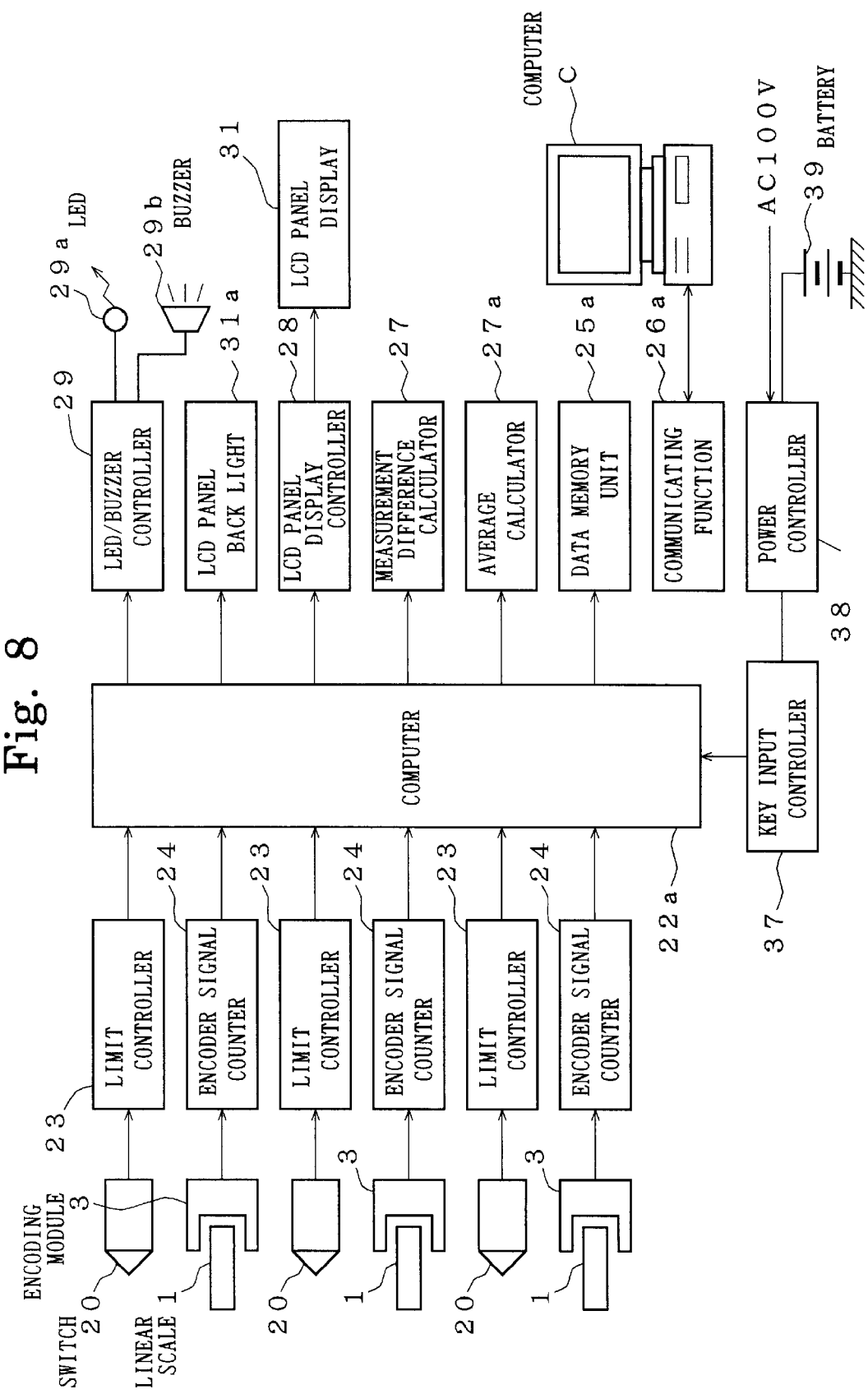
FIG. 8 is a block diagram of an example of an electrical system of the hardness tester of FIG. 6 or 7.
Figure 9:
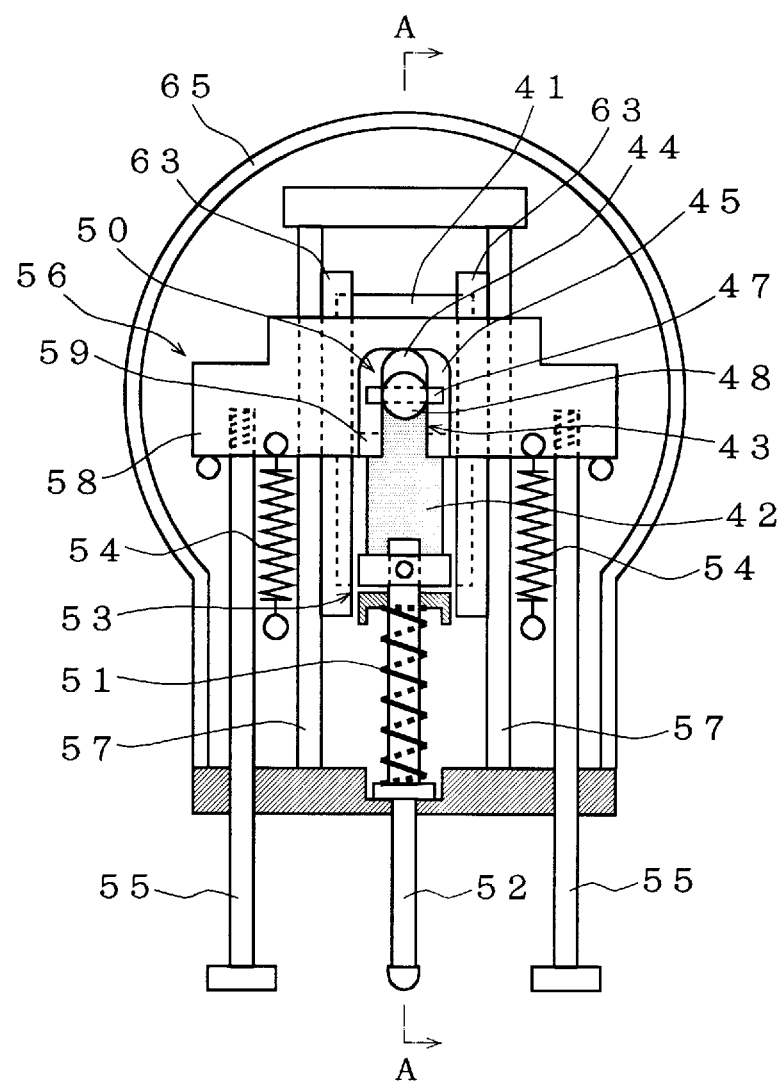
FIG. 9 is a back view of a conventional hardness tester with its back uncovered.
Figure 10:
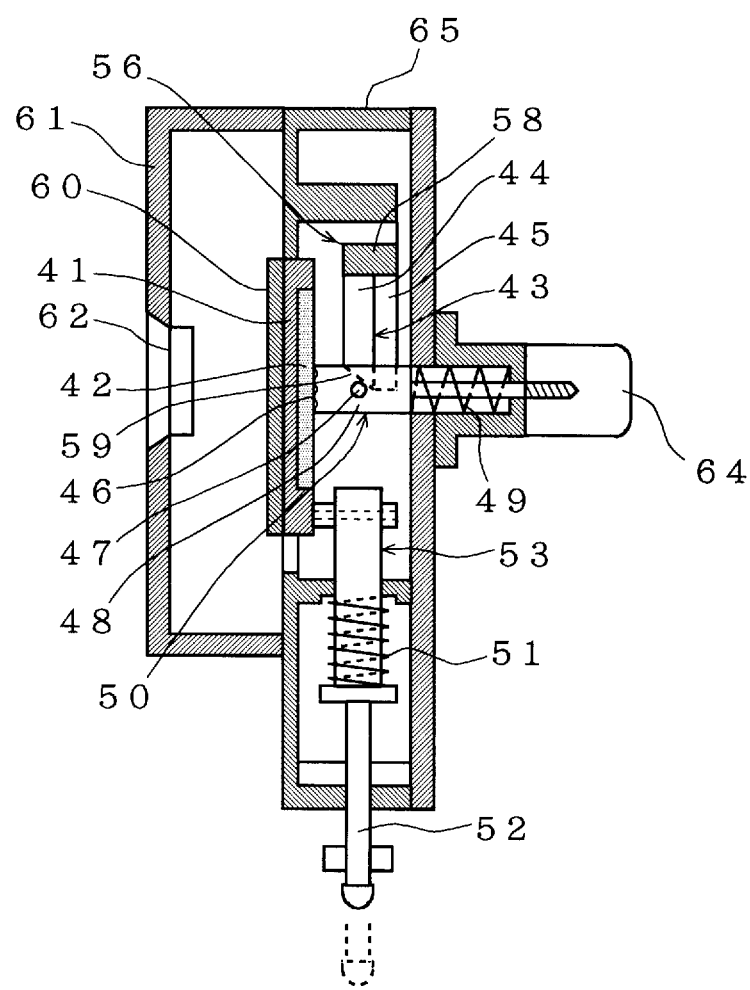
FIG. 10 is a vertical sectional view at the center of the conventional hardness tester, viewed from the side.

FIG. 8 is a block diagram of an example of the electrical system of the hardness tester in the embodiment 2 or 3. The electrical system includes a computer 22a which functions as a data memory unit 25a, the measurement difference calculator 27, an average calculator 27a, the LCD panel display controller 28, an LCD panel back light 31a, the LED/buzzer controller 29, etc. Thus, the computer 22a calculates a hardness based on data of the three (or four) points obtained using three (or four) measurement units each having the indentor 5 and the sleeve 12, and informs the user of the result of the calculation, using the LED 29a, the buzzer 29b and the LCD panel display 31. It is further possible to constitute the computer 22a to have a communicating function 26a so that the computer 22a can communicate with another computer C.

(A) When the hardness of an object point of a muscle is to be measured with the inventive hardness tester, the measurement process is as follows.

After the power key 33 and the key 34 for activating the memory-A 25 are turned on, the indentor 5 and the sleeve 12 are pressed against the muscle 40, as shown FIG. 4, whereby the indentor 5 and the sleeve 12 are pushed upward against the springs. Here, the amount of movement of the sleeve 12 is larger than that of the indentor 5 since the sub spring 17 for the sleeve 12 is weaker than the indentor spring 11 for the indentor 5.

As the indentor 5 moves upward, the linear scale 1 slides upward in the slit of the encoding module 3. When the sleeve 12 has moved a predetermined amount, the amount of movement of the indentor 5 measured by the encoding module 3 is stored in a memory-A 25 and the digital data displayed on the LCD panel display 31 is retained electrically.

(B) When the difference in hardness between the relaxed state and the strained state is to be measured at an object point on a muscle, the measurement process is as follows.

First, the hardness of the object point of the muscle in the relaxed state is measured by the above-described process (A). After that, the key 35 is pushed to activate the memory-B 26, and the indentor 5 and the sleeve 12 are pressed against the muscle in the strained state. Thus, a measurement value corresponding to the strained state is displayed digitally, and the value is stored in the memory-B 26.

After that, when the key 36 is pushed, the measurement difference calculator 27 in the calculation unit 22 is activated, whereby the difference in hardness between the relaxed state and the strained state is calculated and the result of the calculation is displayed on the LCD panel display 31 digitally. The result can be used to estimate the state or condition of the muscle, such as the effects of training, a degree of fatigue, etc.

When the user desires to estimate the effects of training continued for a certain period of time, data for the estimation can be easily obtained by comparing the hardness of the muscle before and after the training.

Thus, the effects of the present invention are as follow.

The hardness of an uneven part of a living body can be measured accurately since the part where the sleeve contacts with the living body is in proximity to the point where the indentor contacts with the living body.

The hardness of an object part of a living body is measured based on an amount of movement of the linear scale detected by the encoding module. The value of hardness is not only displayed on the LCD panel display 31 digitally but also is stored in the memory, and the value on the display is retained electrically. Thus, the system of displaying and retaining the value of hardness is simplified compared to the mechanical system of the conventional hardness tester.

The difference in hardness of an object part of a living body between the relaxed state and the strained state is calculated by the calculation unit automatically, and the result is displayed digitally. Thus, the efficiency of measuring the difference in hardness between the two states is enhanced.

By an inventive hardness tester including a plurality of measurement units wherein the lower ends of the indentors and the sleeves are aligned on the same plane, the efficiency of measuring the average hardness of an area including an object point is improved since hardness of a plurality of points in proximity to the object point are measured at one time by a single measurement operation and the average hardness is calculated automatically. Here, the accuracy of measurement is also improved since all the indentors and the sleeves contact with the surface of the living body at a right angle.

The inventive hardness tester is free of various kinds of mechanical troubles which often occur in conventional hardness testers since the system of displaying and retaining the measurement values do not include mechanical elements such as a stopper pin urged by a compression spring. Of course there is no trouble resulting from the abrasion of a rubber plate. Thus, the accuracy and reliability of measurement are improved.

Accordingly, the present invention has such a pronounced industrial potential usage that it can contribute significantly to the improvement of the physical training in the world of sports or to the improvement of the medical inspection of and treatment to the living body in the medical world.

What is claimed is:

1. A hardness tester for a living body, comprising:
   a) an indentor which is urged by an indentor spring and moves against the indentor spring when pressed against a part of the living body;
   b) a sleeve in which the indentor is inserted and which is urged by a sub spring weaker than the indentor spring and moves against the sub spring when pressed against the part of the living body;
   c) a converter for converting an amount of movement of the indentor into an electrical signal;
   d) a trigger for generating a trigger signal when the sleeve has moved by a predetermined amount; and
   e) a control unit for carrying out a process when receiving the trigger signal, the process including steps of:
      receiving the electrical signal from the converter;
      displaying the amount of movement of the indentor on a display;
      storing the amount in a memory unit;
      calculating a difference in hardness of the part of the living body between a relaxed condition and a strained condition; and
      displaying the difference on the display.

2. The hardness tester according to claim 1, wherein the converter includes a linear scale and an encoder for converting the amount of movement of the indentor into a digital signal.

3. The hardness tester according to claim 1, wherein the converter includes a displacement sensor for measuring the amount of movement based on a change in the capacitance of a condenser.

4. A hardness tester for a living body, comprising a plurality of measurement units, each measurement unit including:
   a) an indentor which is urged by an indentor spring and moves against the indentor spring when pressed against a part of the living body;
   b) a sleeve in which the indentor is inserted and which is urged by a sub spring weaker than the indentor spring and moves against the sub spring when pressed against the part of the living body;
   c) a converter for converting an amount of movement of the indentor into an electrical signal; and
   d) a trigger for generating a trigger signal when the sleeve has moved by a predetermined amount, where the measurement units are combined together so that all the lower ends of the indentors and the sleeves are aligned on the same plane, and the hardness tester further includes:
   e) a control unit for carrying out a process when receiving the trigger signal, the process including steps of:
      receiving the electrical signals from the converters of the measurement units;
      taking an average of the movements of the indentors measured by the measurement units corresponding to the plurality of points in proximity to an object point on the part of the living body;
      displaying the average of movements of the indentors on a display;
      storing the average in a memory unit;
      calculating a difference in hardness of the part of the living body between a relaxed condition and a strained condition; and
      displaying the difference on the display.

5. The hardness tester according to claim 4, wherein the converter includes a linear scale and an encoder for converting the amount of movement of the indentor into a digital signal.

6. The hardness tester according to claim 4, wherein the converter includes a displacement sensor for measuring the amount of movement based on a change in the capacitance of a condenser.

7. A hardness tester for a living body, comprising a plurality of measurement units, each measurement unit including:
   a) an indentor for indenting a part of the living body;
   b) a sleeve in which the indentor is inserted;
   c) an urging mechanism for urging the indentor and the sleeve, where a stress on the indentor is larger than that on the sleeve; and
   d) a calculator for calculating a hardness of the part of the living body based on a difference between a displacement of the indentor and a displacement of the sleeve when pressed against the part of the living body, where the measurement units are combined together so that all the lower ends of the indentors and the sleeves are aligned on the same plane, and the hardness tester further comprising:
   e) an average calculator for taking an average of hardness measured by the measurement units at the plurality of points around an object point at one time.

* * * * *